United States Patent [19]

Nakano et al.

[11] Patent Number: 5,656,736
[45] Date of Patent: Aug. 12, 1997

[54] COMPOUND UCH9

[75] Inventors: Hirofumi Nakano, Machida; Harumi Ogawa, Kawasaki; Yoshinori Yamashita, Machida; Ritsuko Katahira, Yokohama; Shigeru Chiba, Kawasaki; Toshiaki Iwasaki, Sunto-gun; Tadashi Ashizawa, Numazu, all of Japan

[73] Assignee: Kyowa Hakko Kogyo Co., Ltd., Tokyo, Japan

[21] Appl. No.: 424,281

[22] PCT Filed: Jul. 26, 1994

[86] PCT No.: PCT/JP94/01233

§ 371 Date: Apr. 21, 1995

§ 102(e) Date: Apr. 21, 1995

[87] PCT Pub. No.: WO95/06054

PCT Pub. Date: Mar. 2, 1995

[30] Foreign Application Priority Data

Aug. 26, 1993 [JP] Japan .................. 5-211572

[51] Int. Cl.$^6$ .................................................. C07H 15/00
[52] U.S. Cl. ......................... 536/16.8; 536/63; 536/6.4; 536/18.1
[58] Field of Search ..................... 536/4.1, 6.3, 6.4, 536/16.8, 18.1

[56] References Cited

U.S. PATENT DOCUMENTS 3,821,085  6/1974  Zhdanovich et al. ............... 536/16.8

OTHER PUBLICATIONS

Tetrahedron, 1967, vol. 23, pp. 421 to 437.
Biochemistry, 1989, vol. 28, pp. 751 to 762.
Biochemistry, 1993, vol. 32, pp. 463 to 471.
Biochemistry, 1993, vol. 32, pp. 6588 to 6604.

*Primary Examiner*—Elli Peselev
*Attorney, Agent, or Firm*—Antonelli, Terry, Stout & Kraus, LLP

[57] ABSTRACT

The present invention relates to the compound UCH9 represented by the following formula:

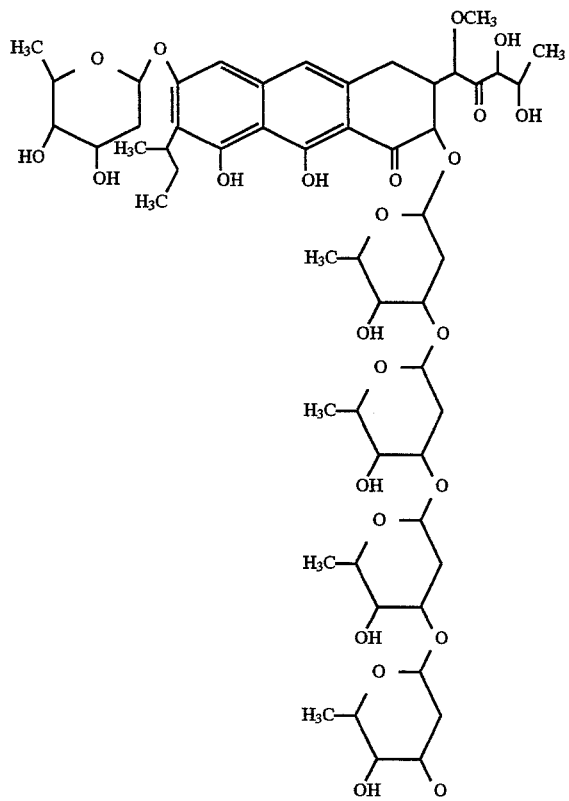

which has antibacterial and anti-tumor activity, and pharmaceutically acceptable salts thereof.

1 Claim, No Drawings

COMPOUND UCH9

TECHNICAL FIELD

The present invention relates to the compound UCH9 which has antibacterial and anti-tumor activity and is useful as antibacterial and anti-tumor agents.

BACKGROUND ART

Heretofore, many compounds such as chromomycin-type compounds, olivomycin-type compounds, and mithramycin-type compounds have been reported as anti-tumor antibiotics belonging to the group of aureolic acids [CRC Handbook of Antibiotic Compounds, CRC Press, vol. 1, 325–348, U.S.A. (1981)].

Chromomycin $A_3$ is known which has a skeleton related to the present compound and which is represented by the following formula (A) [Tetrahedron, 23, 421 (1967)].

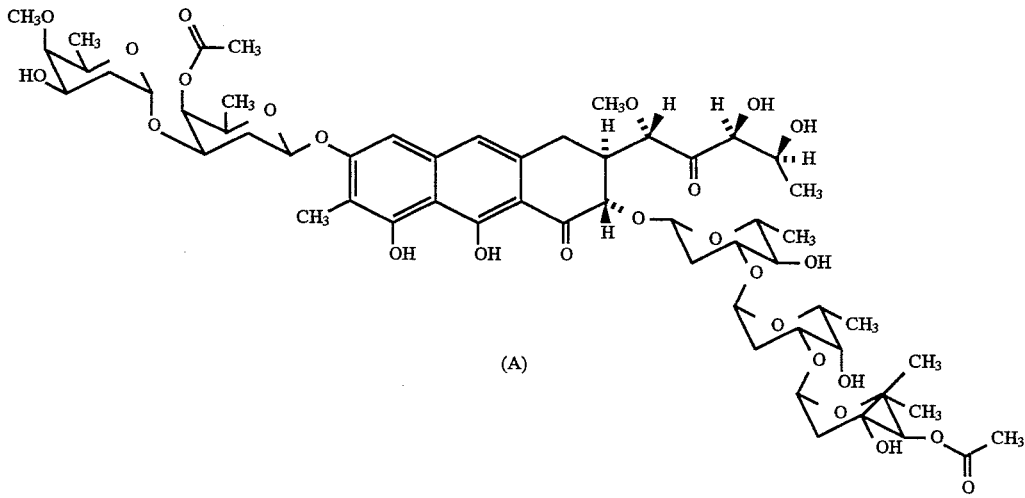

(A)

It is known that these aureolic acids form dimeric complexes having divalent metal ions, e.g., ½ magnesium salt [Biochemistry, 28, 751 (1989); 32, 463 (1993); 32, 6588 (1993)].

DISCLOSURE OF THE INVENTION

The present invention provides the compound UCH9 having antibacterial and anti-tumor activity which is represented by the following formula:

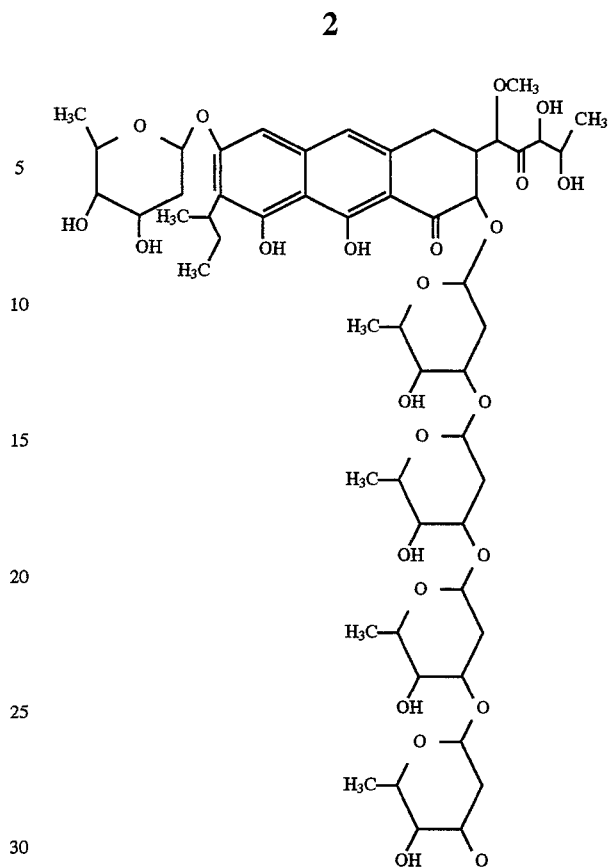

and pharmaceutically acceptable salts thereof.

The pharmaceutically acceptable salts of the compound UCH9 include alkaline earth metal salts such as magnesium salt and calcium salt, nickel salt, etc.

Compound UCH9 forms a dimeric complex having divalent metal ions like other aureolic acids.

Compound UCH9 can be produced by culturing a microorganism belonging to the genus Streptomyces.

The present invention is described in detail below.

The physicochemical properties of UCH9·½ magnesium salt provided by the present invention are shown below.
Physicochemical properties of UCH9·½ magnesium salt
(i) Color and property of the substance:

greenish yellow powder
(ii) Metallic analysis:
  Magnesium was detected by ICP analysis after wet digestion.
(iii) Specific rotation:
  $[\alpha]_D^{23} = +67.2°$ (c=0.125, methanol)
(iv) UV absorption spectrum (measured in methanol):
  $\lambda_{max}$ nm
  $(E_{1cm}^{1\%})$; 232.0(164), 283.5(481), 317.0(62), 418.0(111), 432.5(113)
(v) IR absorption spectrum (measured by the KBr method):
  $\nu_{max}$cm$^{-1}$; 3421, 2933, 1603, 1527, 1373, 1063
(vi) FAB mass spectrum (matrix: m-nitrobenzyl alcohol):
  m/z amu [most abundant mass, calculated for a molecular weight of UCH9 (1126)=M]
  positive mode; 2276.0 (2M−2H+Mg)$^+$, 1149.5 (M+Na)$^+$
  negative mode; 2274.7 (2M−3H+Mg)$^-$, 1125.3 (M−H)$^-$
(vii) High resolution FAB mass spectrum
  (matrix: m-nitrobenzyl alcohol): m/z amu, negative mode
  Found: 1125.5126(M−H)$^-$
  Calculated for $C_{55}H_{81}O_{24}$: 1125.5118
(viii) $^1$H NMR spectrum [500 MHz, CDCl$_3$+CD$_3$OD (3:1) solution]:
  δ ppm (integration) 6.54(1H), 6.39(1H), 5.08(1H), 4.83(1H), 4.70(2H), 4.63(1H), 4.51(1H), 4.38(1H), 4.22(1H), 4.08(1H), 3.99(1H), 3.68(1H), 3.62(3H), 3.60(1H), 3.57(1H), 3.50(1H), 3.48(3H), 3.47(1H), 3.45(1H), 3.42(1H), 3.37(1H), 3.28(1H), 3.16(1H), 3.01(1H), 2.97(1H), 2.83(1H), 2.82(1H), 2.76(1H), 2.64(1H), 2.46(1H), 2.28(1H), 2.16(1H), 2.13(1H), 2.12(1H), 1.85(1H), 1.72(1H), 1.62(1H), 1.52(2H), 1.41(1H), 1.40(3H), 1.38(3H), 1.34(3H), 1.33(3H), 1.32(3H), 1.30(3H), 1.29(3H), 1.28(3H), 0.88(3H)
(ix) $^{13}$C NMR spectrum [125 MHz, CDCl$_3$+CD$_3$OD(3:1) solution]:
  δ ppm (multiplicity) 213.5(s), 196.5(s), 176.4(s), 161.5(s), 160.9(s), 139.3(s), 138.9(s), 116.7(s), 112.5(s), 111.6(s), 110.7(s), 100.8(d), 100.5(d), 100.3(d), 99.9(d), 99.7(d), 95.7(d), 84.8(d), 83.6(d), 82.1(d), 79.6(d), 78.0(d), 77.5(d), 77.4(d), 77.2(d), 75.4(d), 75.3(d), 72.7(d), 72.6(d), 72.4(d), 71.6(d), 71.55(d), 71.4(d), 70.3(d), 67.9(d), 68.1(d), 61.1(q), 59.6(q), 43.1(d), 40.1(t), 39.6(t), 37.3(t), 36.7(t), 32.4(t), 31.5(d), 29.0(t), 28.3(d), 19.7(q), 19.1(q), 18.6(q), 18.4(q), 18.0(q), 17.9(q), 16.6(q), 13.4(q)
(x) Solubility:
  Soluble in dimethylsulfoxide (DMSO) and methanol; sparingly soluble in water and chloroform.
(xi) Color reaction:
  Positive to the iodine test
(xii) Thin layer chromatography:
  silica gel thin layer (HPTLC plate Art. 5715, Merck & Co., Inc.)

The Rf value obtained by using chloroform:methanol:aqueous ammonia (70:26:4 v/v) as a developing solvent was 0.32.

The Rf value obtained by using ethyl acetate:methanol (3:1 v/v) as a developing solvent was 0.67.

The biological activities of UCH9 are described below.
(A) Antibacterial activity against various bacteria The minimum inhibitory concentration (MIC) of the compound obtained in Example 1 against the growth of various bacteria is shown in Table 1.

The antibacterial activity was determined by the agar dilution method using a medium (pH 7) which comprises 3 g/l Bacto-tryptone (Difco Laboratories), 3 g/l meat extract, 1 g/l yeast extract, 1 g/l glucose and 16 g/l agar.

TABLE 1

| Bacteria tested | MIC (μg/ml) UCH9 |
| --- | --- |
| Staphylococcus aureus ATCC 6538P | 5.2 |
| Bacillus subtilis No. 10707 | 0.04 |
| Enterococcus faecium ATCC 10541 | 41.6 |

(B) Growth inhibition against HeLa S$_3$ cells

HeLa S$_3$ cells (ATCC HTB22) were suspended in a medium comprising 10% fetal calf serum, 2 mM glutamine and MEM medium (Nippon Pharmaceutical Co., Ltd.) (hereinafter referred to as medium A) to a concentration of 3×10$^4$ cells/ml. The cell suspension was put into wells of a 96-well microtiter plate in an amount of 0.1 ml per well. The cells in the plate were cultured at 37° C. for 20 hours in a CO$_2$-incubator. Subsequently, the test compound obtained in Example 1 which was appropriately diluted with medium A was added to the wells in an amount of 0.1 ml/well. The cells were further cultured at 37° C. for 72 hours in the CO$_2$-incubator, and then the culture supernatant was removed. To the residue was added a medium comprising medium A and 0.02% Neutral Red in an amount of 0.1 ml per well, followed by culturing at 37° C. for one hour in the CO$_2$-incubator, whereby the cells were stained. After removal of the culture supernatant, the residue was washed once with physiological saline. The pigment was extracted with 0.001N hydrochloric acid/30% ethanol, and the absorbance at 550 nm was measured by using a microplate reader. The concentration of the test compound at which the growth of the cells is inhibited by 50% (IC$_{50}$) was calculated by comparing the absorbance of untreated cells with those of the cells treated with the test compound at known concentrations. The result is shown in Table 2.

TABLE 2

| Test compound | IC$_{50}$ (ng/ml) |
| --- | --- |
| UCH9 | 15 |

The process for producing UCH9 is described below.

UCH9 can be obtained by culturing a microorganism belonging to the genus Streptomyces and having the ability to produce UCH9 in a medium, allowing UCH9 to accumulate in the culture, and recovering UCH9 from the culture.

As the UCH9-producing strains of the present invention, any strains which belong to the genus Streptomyces and have the ability to produce UCH9 can be used. In addition, any mutants of such strains which are obtained by various artificial mutation methods such as UV irradiation, X ray irradiation and treatment with mutagens or by spontaneous mutation may also be used in the present invention, insofar as they have the ability to produce UCH9. A typical example of a suitable strain is UOH9 strain.

The mycological properties of the strain UOH9 are described below.

The properties were studied according to the method recommended by the International Streptomyces Project (ISP) for the characterization of the Streptomyces species [E. B. Shirling and D. Gottlieb: Int. J. Syst. Bacteriol., 16, 313–340 (1966)].

The stereoisomer of diaminopimelic acid in the whole-cell hydrolyzate was identified by the method of B. Becker et al. [Appl. Microbiol., 12, 421–423 (1964)].

The morphological investigations were made under an optical microscope. For spore surface morphology, in particular, a scanning electron microscope was used.

The color names were given according to the Color Harmony Manual (Container Corporation of America, 4th edition, 1958).

1. Morphological characteristics
   1) Mycelium
      Formation of aerial mycelium: Formed
      Fragmentation and motility of aerial mycelium: None
      Fragmentation and motility of substrate mycelium: None
   2) Spore
      Formation and location of spore: Formed on the aerial mycelium
      Formation and location of sporangium: None
      Number of spores in chain formed at the end of the sporophore; 10 or more
      Form of spore chains; Flexuous or spiral chains
      Characteristics of spores:
         Surface; Smooth
         Size; 0.6~0.8×0.8~1.0 μm
         Motility of spore and existence of flagella; None
   3) Others

| | |
|---|---|
| Chlamydospore; | None |
| Synnema; | None |
| Pseudosporangium; | None |

2. Cultural characteristics

The strain UOH9 shows moderate or good growth on synthetic media and natural media which are generally used. The color of the substrate mycelia is pale yellow to brown. Formation of soluble brown pigment was observed on some of the culturing media.

The cultural characteristics such as growth and color of UOH9 strain on various agar media observed after culturing at 28° C. for 14 days are shown below.

1) Malt extract—yeast extract agar medium
   Degree of growth; Moderate
   Color of substrate mycelium; Light gold (2 ic)
   Formation of aerial mycelium and its color; Poor, oyster white (b)
   Formation of soluble pigment; None
2) Oatmeal agar medium
   Degree of growth; Poor
   Color of substrate mycelium; Bamboo (2 gc)
   Formation of aerial mycelium and its color; None
   Formation of soluble pigment; Observed
3) Starch—inorganic salts agar medium
   Degree of growth; Moderate
   Color of substrate mycelium; Cream (1 ½ ca)
   Formation of aerial mycelium and its color; None
   Formation of soluble pigment; None
4) Glycerol—asparagine agar medium
   Degree of growth; Moderate
   Color of substrate mycelium; Light ivory (2 ca)
   Formation of aerial mycelium and its color; None
   Formation of soluble pigment; None 3. Physiological characteristics The physiological characteristics of UOH9 strain are shown below. Growth temperature range was determined after 5 days of culturing and the other observations were made after 2 to 3 weeks of culturing at 28° C.

1) Growth temperature range; 15°~47° C.

2) Production of melanin-like pigment
   (i) Peptone—yeast—iron agar medium; Positive
   (ii) Tyrosine agar medium; Negative
3) Assimilability of carbon sources
(As the basis medium, Pridham Gottlieb agar medium was used.)

| | |
|---|---|
| L-Arabinose; | Assimilable |
| D-Xylose; | Assimilable |
| D-Glucose; | Assimilable |
| Sucrose; | Assimilable |
| Raffinose; | Nonassimilable |
| D-Fructose; | Assimilable |
| Rhamnose; | Assimilable |
| Inositol; | Assimilable |
| D-Mannitol; | Assimilable |

4. Chemotaxonomic characteristics

Configuration of diaminopimelic acid in whole-cell hydrolysate; LL-form

The strain UOH9 is classified in the Type I cell wall group (LL-diaminopimelic acid, glycine) from the above chemotaxonomic characteristics according to the classification of actinomycetes by M. P. Lechevalier and H. A. Lechevalier [Int. J. Syst. Bacteriol., 20, 435–443 (1970)]. On the basis of this characteristic and the morphological characteristics, i.e. formation of spore chains on aerial mycelia, it is reasonable to regard the strain as belonging to the genus Streptomyces.

For species identification within the genus, a search was made through the Approved Lists of Bacterial Name [V. B. D. Skerman et al.: Int. J. Syst. Bacteriol., 30, 225–420 (1980)] for a species having taxonomical characteristics akin to those of UOH9 strain according to the descriptions given by the ISP [Int. J. Syst. Bacteriol., 18, 69–189 (1968); ibid., 18, 279–392 (1968); ibid., 19, 391–512 (1969); ibid., 22, 265–394 (1972); and R. E. Buchanan and N. E. Gibbons (eds.): Bergey's Manual of Determinative Bacteriology, 8th edition]. The search was made on the basis of the following characteristics of UOH9 strain: gray to white aerial mycelium, flexuous or loop-like spore chains, smooth spore surface, melanin-like pigment production, soluble pigment production, and carbon source assimilability pattern. According to the search results, it was difficult to identify the species of the present strain, and the present strain was named Streptomyces sp. UOH9.

The strain has been deposited with the National Institute of Bioscience and Human-Technology, Agency of Industrial Science and Technology with accession number FERM BP-4392 under the Budapest Treaty (date of original deposit: Aug. 24, 1993).

The culturing method for the UCH9-producing strains is as follows.

For the culturing of the UCH9-producing strains used in the present invention, conventional methods for culturing actinomycetes are generally employed. As the medium, either a synthetic medium or a natural medium may be used insofar as it appropriately contains carbon sources, nitrogen sources and inorganic substances which can be assimilated by the strains employed and the growth-and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed.

As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination.

If necessary, inorganic salts such as sodium chloride, potassium chloride, magnesium sulfate, calcium carbonate, potassium dihydrogen phosphate, ferrous sulfate, calcium chloride, manganese sulfate, zinc sulfate, and copper sulfate may be added. In addition, trace ingredients that promote the growth of the strain employed and the production of UCH9 may also be added to the medium.

As the method of culturing, liquid culture, especially submerged stirring culture, is preferably employed. Culturing is carried out at 16° to 37° C., preferably 25° to 32° C., and at pH 4 to 10, preferably 6 to 8. In general, by culturing for 1 to 7 days, the desired compound UCH9 is produced and accumulated in the culture broth and the microbial cells. In order to adjust the pH of the medium, aqueous ammonia, ammonium carbonate solution, etc. are used. When the amount of the product in the culture reaches the maximum, the culturing is discontinued.

For the isolation and purification of the desired compound UCH9 from the culture, an ordinary method for isolating a microbial metabolite from the culture can be utilized. For example, the culture is separated into culture filtrate and microbial cells by filtration. The microbial cells are extracted with chloroform, acetone, or the like. Then, the extract is mixed with the culture filtrate, and the resulting mixture is passed through a column of polystyrene adsorbent such as Diaion HP20® (Mitsubishi Kasei Corporation) to adsorb the active substance, followed by elution with ethyl acetate, acetone, or the like. The eluate is concentrated, and the concentrate is subjected to silica gel column chromatography, high performance liquid chromatography, and the like to give UCH9. During the culture and purification steps, UCH9 can be traced by bioassay using *Bacillus subtilis* No. 10707, or by monitoring of the UV absorbance of UCH9 in thin layer chromatography.

BEST MODE FOR CARRYING OUT THE INVENTION

Example 1

Streptomyces sp. UOH9 strain (FERM BP-4392) was used as the seed strain. The strain was inoculated into 300 ml of a seed medium having the following composition in a 2-l Erlenmeyer flask, and cultured with shaking (rotation: 200 rpm) at 28° C. for 24 hours.

Composition of the seed medium: 5 g/l Bacto-tryptone (Difco Laboratories), 5 g/l yeast extract, 3 g/l meat extract, 10 g/l soluble starch, 10 g/l glucose and 5 g/l calcium carbonate (pH 7.2 before sterilization)

The resulting seed culture was transferred into 15 l of a fermentation medium having the following composition in a 30-l jar fermentor in an amount of 10% of the fermentation medium (by volume), and culturing was carried out at 28° C. with stirring and aeration (rotation: 225 rpm, aeration: 15 l/min.).

Composition of the fermentation medium: 5 g/l soluble starch, 1 g/l yeast extract, 0.5 g/l $KH_2PO_4$, 0.5 g/l $MgSO_4 \cdot 7H_2O$, 0.5 g/l $Mg_3(PO_4)_2 \cdot 8H_2O$ (pH 7.0 before sterilization, adjusted with NaOH)

Culturing was carried out for 144 hours without controlling the pH of the medium. After the completion of culturing, 15 l of isopropanol was added to the culture, followed by stirring. The removal of the cells and precipitates by filtration gave 28 l of a filtrate. The filtrate was concentrated, and the concentrate was diluted with water. The resulting mixture was passed through a column packed with 10 l of a polystyrene adsorption resin, Diaion HP20® to adsorb the active substance. After impurities were eluted succesively with deionized water and 50% methanol, the active substance was eluted with 80% methanol. The active fraction thus eluted was concentrated and water was added to the concentrate, followed by extraction with ethyl acetate. The extract was dried over sodium sulfate, and concentrated. The residue was applied to a silica gel column (BW300, Fuji Davison Chemical Co., Ltd.) and developed with chloroform:methanol solution (4:1 v/v). The active fraction thus eluted was concentrated, and the concentrate was applied to a gel filtration column (Sephadex LH-20; Pharmacia) and developed with 70% methanol. The active fraction eluted was concentrated to give 4.4 mg of UCH9·½ magnesium salt as greenish yellow powder.

Industrial Applicability

According to the present invention, the compound UCH9 which has antibacterial and anti-tumor activity and pharmaceutically acceptable salts thereof can be provided.

We claim:

1. An isolated and purified compound UCH9 which is represented by the following formula:

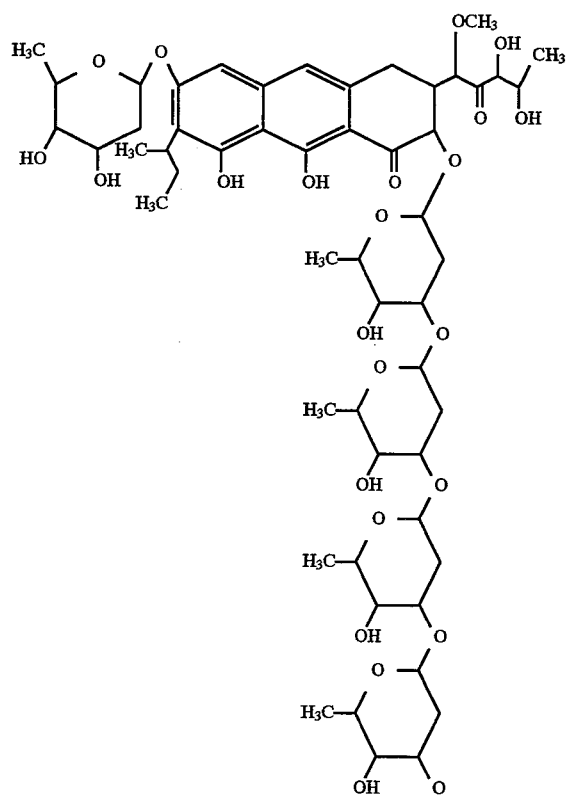

or a pharmaceutically acceptable salt thereof.

* * * * *